United States Patent [19]

Bycroft et al.

[11] Patent Number: 5,043,176
[45] Date of Patent: Aug. 27, 1991

[54] SYNERGISTIC ANTIMICROBIAL COMPOSITIONS

[75] Inventors: Nancy L. Bycroft, Constantine, Mich.; Graham S. Byng; Stephen R. Good, both of Elkhart, Ind.

[73] Assignee: Haarmann & Reimer Corp., Springfield, N.J.

[21] Appl. No.: 537,463

[22] Filed: Jun. 13, 1990

[51] Int. Cl.$^5$ .............................................. A23B 7/155
[52] U.S. Cl. ..................................... 426/335; 426/56; 426/63
[58] Field of Search .................... 426/332, 92, 335, 63, 426/56, 57, 59, 654, 652, 133, 135, 140, 9; 134/25.1, 25.2, 25.3

[56] References Cited

U.S. PATENT DOCUMENTS 4,597,972  7/1986  Taylor ..................................... 426/9

OTHER PUBLICATIONS

Somers 1981 J Food Science 46:1972.
Chemical Abstracts 1986, vol. 104:128479w.
Scott 1981 J Food Science 46:121.
Chemical Abstracts 1990, vol. 111:38169k.
Scott 1981 J Food Science 46:118.
Delves-Broughton 1990 Food Technology Nov., p. 100.
Chemical Abstracts 1990, vol. 113:96287z.
Chemical Abstracts 1990, vol. 112:95145u.

*Primary Examiner*—Carolyn Paden
*Attorney, Agent, or Firm*—Mary G. Boguslaski

[57] ABSTRACT

The invention discloses an antimicrobial composition composed of an antimicrobial polypeptide and a hypothiocyanate component. Synergistic activity is seen when the composition is applied at between about 30 and 40 degrees Centigrade at a pH between about 3 and about 5. The composition is useful against gram negative bacteria such as Salmonella. A preferred composition is nisin, lactoperoxidase, thiocyanate and hydrogen peroxide. Such a composition is capable of reducing the viable cell count of Salmonella by greater than 6 logs in 10 to 20 minutes.

13 Claims, No Drawings

SYNERGISTIC ANTIMICROBIAL COMPOSITIONS

FIELD OF THE INVENTION

The invention relates to antimicrobial compositions in general, and, more particularly, to synergistic combinations of a hypothiocyanate component and an antimicrobial polypeptide which combinations are cidal against gram negative bacteria. Preferred combinations include a hypothiocyanate component composed of a peroxidase, thiocyanate and peroxide and an antimicrobial polypeptide chosen from the group consisting of a cecropin, a sarcotoxin, a combination of magainin I and II and lantibiotics such as nisin, Pep 5, colicin E1 and subtilin. Most preferred is a composition of nisin, lactoperoxidase, peroxide and thiocyanate.

BACKGROUND OF THE INVENTION

The lactoperoxidase system (LPS) is a well known antimicrobial system and is composed of lactoperoxidase, thiocyanate and hydrogen peroxide. The system occurs naturally in milk. Although the mechanism of action is not completely understood, it is postulated that the system catalyses the oxidation of thiocyanate to hypothiocyanate and that the active antimicrobial is hypothiocyanate. Although LPS is known to affect gram negative organisms such as Salmonella, the effect has been shown to require 3 to 4 hours of contact. European Patent Application, Publication No. 0 252 051, assigned to EWOS Aktieboieg, discloses that the addition of an acid to adjust the pH of the lactoperoxidase enzyme in the dry state to between 3 and 5 increases the storage stability of the enzyme.

In PCT application, International Publication No. WO 88/02600, Poulsen discloses a bacteriocidal composition composed of lysozyme, peroxidase, a hydrogen peroxide forming enzyme and thiocyanate used for dental and wound treatment preparations. Lactoperoxidase is preferred. The composition was tested against Streptococcus, Lactobacillus, Bacteroides, Flavobacterium and Fusobacterium; all gram positive bacteria. Bacterial growth was reported to cease upon addition of the composition.

Nisin is the best known polypeptide of the lantibiotic group and is a well known, food acceptable, antimicrobial. However, although nisin is widely known to have an inhibitory effect on grampositive bacteria. It is generally believed to have no inhibitory effect on gramnegative bacteria. U.S. Pat. Nos. 4,597,972 and 4,584,199, assigned to Aplin and Barrett, disclose the use of 2000 to 10,000 International Units of nisin to prevent the outgrowth of spores of *Clostridium botulinum* in processed foods and food products.

Antimicrobial compositions which include synergistic amounts of two or more antimicrobials have been reported previously. PCT application, International Publication No. WO 89/12399, assigned to the Public Health Research Institute of the City of New York, discloses combinations of lantibiotics, such as nisin, and a chelating agent provide enhanced activity and a broader spectrum of activity on both gram negative and gram positive organisms.

Synergistic combinations of lysozyme and cecropins or sarcotoxin have been reported to lyse or inhibit eucaryotic cells in PCT application, International Publication No. WO 89/00194, assigned to the Louisiana State University Agricultural and Mechanical College. The disclosure states that the activity of a lytic polypeptide such as a cecropin or sarcotoxin may be enhanced by combination with lysozyme. Such synergistic combinations may be used not only to lyse or inhibit eucaryotes, but also bacteria, and that use applications suggested include use in food stuffs and other products as an antibacterial preservative and in agricultural application, for example, in a spray applied in an effective amount to crops to prevent infection by, or to inhibit plant pathogens.

Previous work commonly assigned herein, has found that nisin and lysozyme provide a synergistic antimicrobial combination against bacteria, particularly Listeria.

There have been no reports to date on the activity of a combination of the two antimicrobial systems, lactoperoxidase and nisin.

The synergistic antimicrobial composition of this invention has been found to be an effective cidal agent against the gram-negative organisms, such as Salmonella, in a much shorter time period than the lactoperoxidase system alone. As such it will be useful to eliminate surface contaminations of food products and as a disinfectant for food processing plants.

SUMMARY OF THE INVENTION

The invention described herein provides an antimicrobial composition composed of an antimicrobial polypeptide, a hypothiocyanate component and a buffering component capable of providing a pH between about 3 and about 5. Synergistic activity is seen against gram negative organisms when the composition is applied at between about 30 and 40 degrees Centigrade. A preferred hypothiocyanate component is lactoperoxidase, thiocyanate and a peroxide. Also provided are a methods of use and a method of producing the antimicrobial composition. The composition is particularly useful on surfaces, fresh produce, fish and meat such as poultry.

DESCRIPTION OF THE INVENTION

The synergistic antimicrobial composition of the invention is composed of an antimicrobial polypeptide, a hypothiocyanate component, and a buffering component capable of providing a pH between about 3 and about 5. It has been found that a preferred composition (nisin, lactoperoxidase, thiocyanate and hydrogen peroxide) is capable of decreasing the viable count of *Salmonella typhimurium* by greater than six logs in twenty minutes.

A composition was considered to be an "effective" antimicrobial only if a reduction of viable cell count of 3 logs or greater was seen 45 minutes after the antimicrobial composition was applied. Testing used indicated cidal activity (bacterial killing) rather than static activity. The concentration of nisin in the antimicrobial composition, when used alone, had limited cidel effect in the same amount of time under the same conditions and the lactoperoxidase system alone provided a viable count reduction of only one log in the same amount of time, under the same conditions. Compositions of this invention were deemed to be "synergistic" when the effect of the composition in the same time frame and under the same conditions was greater than the additive effect of the components alone.

Although the lactoperoxidase system has been reported to have an inhibitory effect on gram-negative bacteria, the effect seen with the addition of nisin is dramatically greater in a much shorter time frame.

COMPOSITION

An antimicrobial polypeptide is defined herein as a molecule containing between 3 and 50 amino acids, preferably 8 to 34. Examples of such polypeptides are magainin I and magainin II, cecropins, sarcotoxins and lantibiotics such as nisin, subtilin, colicin E1, PEP-5 and pediocin. Preferred polypeptides are magainins and lantibiotics; most preferred is the lantibiotic, nisin. This definition of antimicrobial polypeptide does not include lysozyme which is an enzyme and much larger than the polypeptides contemplated for use herein.

Nisin as used herein refers to a purified preparation of the nisin obtained from Sigma Chemical Company. A purification procedure is provided in the Examples.

As used herein the phrase "hypothiocyanate component" is considered equivalent to hypothiocyanate or a hypothiocyanate generating system. The hypothiocyanate component is defined herein as any composition which is capable of generating the antimicrobially active component of the lactoperoxidase system. This component is commonly believed to be hypothiocyanate. One system capable of generating hypothiocyanate is composed of a peroxidase, thiocyanate and a peroxide. The phrase "lactoperoxidase system", as used herein, refers to a combination of lactoperoxidase, hydrogen peroxide and thiocyanate and is abbreviated as LPS in the tables.

The hypothiocyanate component may include any peroxidase provided that it is capable of catalysing the reaction between the peroxide and thiocyanate. For example horseradish peroxidase, lactoperoxidase or chloroperoxidase may be used. Lactoperoxidase is available commercially from Sigma Chemical Company and is the peroxidase of choice for food systems of interest because of its natural occurrence in milk.

Any thiocyanate salt may be used although common alkali metal salts such as sodium and potassium thiocyanates are preferred. Sodium thiocyanate may also be obtained from Sigma.

The term "peroxide" commonly refers to hydrogen peroxide although other peroxides with the same activity may be used. A peroxide generating system may also be used. Peroxide generating systems such as a combination of glucose and glucose oxidase are well known in the art. Although hydrogen peroxide is well known to have some antimicrobial activity, and is commonly sold in drugstores in a 3% (volume/volume) strength, the concentration of hydrogen peroxide needed to act with peroxidase and thiocyanate to produce antimicrobial activity is about one ten thousandth (1/10000) of that concentration.

The buffering component may be any of those which are capable of providing buffering capacity between the pH of about 3 to 5. Suitable buffers include phosphate, citrate and acetate. As described in the Examples, phosphate is a preferred buffer. However, there are many buffer systems available which are well known to those of skill in the art which may be used as long as there is no interference with the generation of hypothiocyanate.

Method of Preparation:

The composition is prepared by mixing the ingredients and warming the pH adjusted mixture to between 30° and 40° degrees Centigrade. This method is considered equivalent to mixing antimicrobial peptide and hypothiocyanate component, warming, adding a buffer solution and warming or adding a warmed buffer solution. Solutions of the individual components prior to mixing ma also be warmed prior to mixing.

A synergistic increase in effectiveness of the ingredients of the antimicrobial composition is seen between a pH of about 3 and a pH of about 5. Within this pH range, it is possible to use less nisin than is required for a similar effect above pH 5 and less hypothiocyanate such as a lactoperoxidase system than is required for a similar effect below pH 3. Most of the work disclosed herein was done at a pH of 3.6 in order to provide a consistent results for comparison.

In order to provide the most effective antimicrobial system for short term effectiveness, the mixture should be mixed and heated to a temperature of between about 30° and 40° C. prior to use, preferably at least about 35° C. This is a particularly advantageous temperature for application to freshly slaughtered poultry because the composition is brought to a temperature similar to that of the poultry and therefore the application of the composition will not close the pores on the poultry skin which closing may effectively protect undesirable bacteria from contact with the antimicrobial composition.

The antimicrobial composition is most preferably heated to a temperature of about 37° C. prior to contact with a contaminated surface. Although the mechanism of action of the lactoperoxidase system in combination with an antimicrobial polypeptide, is not known, it is speculated that this temperature provides for the generation of the active antimicrobial component of the lactoperoxidase system. This active component may be hypothiocyanate.

In addition it was found that the best results were found when the order of mixing the antimicrobial composition components was: antimicrobial polypeptide, thiocyanate, peroxide and then peroxidase.

In use, the concentrations of the components may be varied to achieve the desired effect in the desired time frame. However, it was found that with a pH of about 3.6 and with warming to about 37° C. prior to contact with the organisms; there was a decrease of six logs in viable count of $S.$ $typhimurium$ in twenty minutes (1 million fold).

A synergistic antimicrobial solution may be generated at the site of use by passing a solution of thiocyanate and peroxide over immobilized peroxidase to produce hypothiocyanate (J. General Microbiology, 1980, 120, 513–516.) and combining the hypothiocyanate produced with an antimicrobial polypeptide (for example between about 2000 IU/mL and 20,000 IU/mL nisin) to produce an antimicrobial solution. The pH of the antimicrobial solution may be adjusted with a suitable buffer and warmed to between about 30 and 40 degrees centigrade prior to application or the individual components may be pH adjusted and warmed.

Application:

The composition may be used as a disinfectant for cleaning surfaces and cooking utensils in food processing plants and any area in which food is prepared or served such as hospitals, nursing homes, restaurants, especially fast food restaurants, delicatessens and the like. It may also be used as an antimicrobial in food products and would be particularly useful as a surface antimicrobial on cheeses, fresh produce such as fruits and vegetables and foods on salad bars and in delis. The composition may be applied by contacting the surfaces of the food by spraying, dipping or the like. It is also expected that the composition will be mixed with food.

One application of particular interest is the decontamination of freshly slaughtered poultry. It is well known that poultry carry Salmonella in their feces and on their skins to the slaughter house. It is particularly important to eradicate this contaminant early in processing. The freshly slaughtered poultry in the processing line may be sprayed or immersed into a solution of the antimicrobial composition prior to the poultry being immersed in the chill tank. Because of the short time to produce effective bacteriocidal action, the time of the processing line need not be increased. Ten to twenty minutes of contact with the poultry surfaces prior to immersion in the chill tank would be sufficient to kill contaminating Salmonella. The ingredients of the composition could be held in tanks with an immobilized peroxidase heated to between about 30° and 40° C. The thiocyanate and hydrogen peroxide would then be passed over the immobilized peroxidase providing the five minute incubation period to produce the active antimicrobial. The hypothiocyanate containing solution would then be mixed with a solution of antimicrobial polypeptide, also at a temperature of between about 30° and 40° C., and the resultant antimicrobial solution would be sprayed on the poultry as the carcasses move continuously through processing. Either or both solutions could be adjusted to a pH of between about 3 and 5.

DESCRIPTION OF THE PREFERRED EMBODIMENT

It has been found that the use of a synergistic composition composed of lactoperoxidase, peroxide, thiocyanate and nisin, provides a broader spectrum of action and a decreased time of effectiveness. The synergistic antimicrobial composition of the invention provides bacteriocidal activity in gram negatives such as *E. coli* and Salmonella in less than about one hour. Of particular interest is killing gram negative food pathogens, especially *Salmonella typhimurium* and *Salmonella enteritidis*.

Preferred compositions utilizing nisin as the antimicrobial peptide contain between about 2000 and about 20,000 International Units per milliliter.

The following examples disclose preferred embodiments of the invention, but do not limit the applicability of the invention which is solely defined by the claims.

EXAMPLES

Example One—Effect of nisin and hypothiocyanate on *Salmonella typhimurium*.

Growth Conditions

*Salmonella typhimurium* (ATCC 14028) was maintained on an agar medium containing tryptic soy agar (Difco Labs). Stock agar slants were stored at 4° C. An overnight culture of *S. typhimurium* was prepared by inoculating a 250 mL flask containing 10 mL nutrient broth with 1 loop of culture from the stock slant and incubating at 37° C. with slow shaking at 25 rpm on a New Brunswick G24 shaker. The overnight grown culture was then used to inoculate fresh nutrient broth (1:20 inoculation level) in a 250 mL side arm flask. This flask was then incubated at 37° C., and agitated at 25 rpm until the culture reached a density of 100 units as measured using a Klett-Sommerson photometer. This density corresponded to a viable cell count of approximately $3 \times 10^8$ cells per mL. All testing was done on cells at log phase growth unless otherwise indicated.

Purification of commercially available nisin.

Nisin obtained from Sigma was purified to remove impurities consisting primarily of sodium chloride and denatured milk solids.

Nisin was dissolved in water and the pH adjusted to 2.5 with hydrochloric acid. The solution was diafiltered to remove sodium chloride. The filtrate was heated to 80° C. to coagulate and precipitate the milk solids; a filter aid such as diatomaceous earth was added; and the filtrate was vacuum filtered to remove the precipitated milk solids. Optionally the pH of the filtrate may be adjusted to 6 before vacuum filtering to obtain even higher purity. Preparations obtained in either manner were bacteriocidal against gram negative bacteria. The solution obtained contained purified nisin. The solution was assayed by the standard method and activity assigned in that way.

Nisin-Lactoperoxidase System

An antimicrobial composition of nisin and a hypothiocyanate component consisting of sodium thiocyanate, hydrogen peroxide and lactoperoxidase (referred to herein as the lactoperoxidase system and abbreviated in the tables as LPS) was prepared by addition of the ingredients in the following order:

| | |
|---|---|
| Nisin | 0 to 20,000 units/mL |
| Sodium thiocyanate | 1.5 mM |
| Hydrogen peroxide | 0.5 mM |
| Lactoperoxidase | 0.24 units/mL | was added to 9 mL of 0.2% (w/v) $KH_2PO_4$ in deionized water adjusted to pH 3.6 with hydrochloric acid (all concentrations are given for a final concentration in 10 mL of reaction mixture). Although this order of mixing appears to give the best results, it is not required to produce a synergistic antimicrobial solution.

The system was incubated for 5 minutes at 37° C. with gentle agitation (25 rpm) followed by inoculation with 1 mL of the culture of *S. typhimurium*, obtained as described previously, containing $10^8$ cells per milliliter. Incubation was continued at 37° C. and samples were withdrawn at 10 and 20 minute intervals. Serial dilutions were carried out in nutrient broth and viable counts were obtained following growth of samples on nutrient broth plates with incubation at 37° C. for 48 hours.

Results

| Nisin Concentration | $Log_{10}$ Reduction in Viable Count | |
|---|---|---|
| (units/mL) | 10 minutes | 20 minutes |
| 0 | 0 | 1 |
| 2,000 | 0 | 2.4 |
| 4,000 | 0 | 1 |
| 6,000 | 0 | 2 |
| 8,000 | 0 | 3 |
| 10,000 | 0 | 3 |
| 16,000 | 0 | >6 |
| 20,000 | 2.8 | >6 |
| 2,000 nisin no LPS | 0 | 0 |
| 20,000 nisin no LPS | 0 | 0 |

As seen above, LPS alone provided one log reduction in viable count in 20 minutes and between 2,000 International Units (abbreviated "units" herein) nisin alone per milliliter provided no reduction in viable count. However, the composition of this invention including 16,000 to 20,000 units nisin provided greater than six logs reduction in twenty minutes against *S. typhimurium*.

Example Two: Effect of nisin and hypothiocyanate on *Salmonella enteritidis*.

*Salmonella enteritidis* (ATCC 13076) was prepared as disclosed in Example 1 and maintained on an agar medium containing tryptic soy agar (Difco Labs). The antimicrobial composition containing nisin and the lactoperoxidase system was prepared as disclosed in Example 1.

Results

|  | Log reduction in viable count | | |
| --- | --- | --- | --- |
|  | 10 | 20 minutes | 30 |
| 2,000 units/mL nisin + LPS | 6 | >6 | >6 |
| 20,000 units/mL nisin + LPS | >6 | >6 | >6 |
| LPS alone | 2.11 | 5.08 | >6 |
| 2,000 units/mL nisin (no LPS) | 0 | 2 | 2.55 |
| 20,000 units/mL nisin (no LPS) | 2.09 | 2.21 | 2.55 |

Synergy was seen by increased reduction in viable count at 10 minutes. At 20 minutes and longer, LPS was so effective against *S. enteritidis* that no synergistic effect was discernible since the maximum viable count was 10 8.

Example Three: The effect of eliminating preincubation from the preparation of the antimicrobial solution.

A culture of *S. typhimurium*. was obtained as described in Example 1. The antimicrobial composition was also prepared as described in Example 1. One set of samples was tested as shown in Example 1. A second set was inoculated with 1 mL culture immediately after the ingredients were added, eliminating preincubation.

Results

|  | Preincubation | Log reduction in viable count | | |
| --- | --- | --- | --- | --- |
|  |  | 10 | 20 | 30 |
| 20,000 units/mL nisin + LPS | yes | 0 | 6 | >6 |
| + LPS | no | >6 | >6 | >6 |
| + LPS | yes | 0 | 0 | 0 |
|  | no | 0 | 2.17 | 6 |
| 20,000 IU/mL | yes | 0 | 0 | 0 |
| nisin | no | 0 | 0 | 0 |

The experiment indicated that the antimicrobial composition is more effective than would be expected from the additive effects of the same amount of nisin and the same LPS for the same period of exposure, even when the preincubation was eliminated.

Example Four: The use of a combination of Magainin I and II as the antimicrobial polypeptide.

A culture of *Salmonella typhimurium*, ATCC 14028, was prepared as described in Example 1. An antimicrobial solution was prepared using Magainin I and II as the antimicrobial polypeptide and the lactoperoxidase system:

The antimicrobial composition was prepared by addition of the ingredients in the following order:

| magainin I | 1000 nanograms/mL |
| --- | --- |
| magainin II | 1000 nanograms/mL |
| Sodium thiocyanate | 1.5 mM |
| Hydrogen peroxide | 0.5 mM |
| Lactoperoxidase | 0.24 units/mL | to 9 mL of 0.2% (w/v) $KH_2PO_4$ in deionized water adjusted to pH 3.6 with hydrochloric acid (all concentrations are given for a final concentration in 10 mL of reaction mixture).

The antimicrobial solution was incubated for 5 minutes at 37° C. with gentle agitation (25 rpm) followed by inoculation with 1 mL of the culture described previously, containing $10^8$ cells per milliliter *S. typhimurium*. The solution was treated and tested as described in Example 1. Control solutions of Magainin I/II alone were prepared by adding 1000 nanograms/mL magainin I and 1000 nanograms/mL magainin II to 9 mL of 0.2% (w/v) $KH_2PH_4$ in deionized water adjusted to pH 3.6 with hydrochloric acid. The system was incubated for 5 minutes, treated and tested as described previously.

Results

|  | Log reduction in viable count | | | |
| --- | --- | --- | --- | --- |
|  | 20 | 30 | 40 minutes | 60 |
| Magainin I, II + LPS | 1.99 | 2.10 | 2.03 | 2.33 |
| Magainin I, II | 0.4 | 0.22 | 0.36 | (0.12) |
| LPS | 1.7 | 0.93 | 2.20 | 2.36 |

An increase in effectiveness over an effect expected from the results of the use of the combination Magainin I/II alone or LPS alone, was seen at 30 minutes.

Example Five: The use of Colicin E1 as the antimicrobial polypeptide.

A culture of *S. typhimurium*. was prepared as described in Example 1. An antimicrobial solution containing colicin E1 as the antimicrobial polypeptide and the lactoperoxidase system as the hypothiocyanate component was prepared by adding (in order):

| Colicin E1 | 5000 nanograms/mL |
| --- | --- |
| Sodium thiocyanate | 1.5 mM |
| Hydrogen peroxide | 0.5 mM |
| Lactoperoxidase | 0.24 units/mL | to 9 mL of 2.0% (w/v) $KH_2PO_4$ in deionized water adjusted to pH 3.6 with hydrochloric acid (all concentrations are given for a final concentration in 10 mL of reaction mixture).

Colicin E1 was added to 9 mL 0.2% (w/v) $KH_2PO_4$ in deionized water, adjusted to pH 3.6 with hydrochloric acid, without sodium thiocyanate, hydrogen peroxide, and lactoperoxidase, was used as a control.

The systems were incubated at 37° C. and tested as described previously.

Results

|  | Log$_{10}$ Reduction in Viable Count | | |
| --- | --- | --- | --- |
|  | 20 | 40 minutes | 60 |
| Colicin El + LPS | 0.79 | 6.52 | 6.52 |
| Colicin | 0.12 | (0.08) | (0.26) |
| LPS | 0.74 | 4.18 | 6.52 |

The results indicate that with 40 minutes exposure, the effect of the antimicrobial composition was greater than the additive effect of the individual components.

Example Six: Use of the antimicrobial composition against log phase *E. coli* and stationary phase *E. coli*.

*E. coli* (log phase)

*Escherichia coli*, ATCC 8739, was maintained on an agar medium containing tryptic soy agar (Difco Labs). Stock agar slants were stored at 4° C. Culture for testing was obtained as described in Example 1. The dilution tested contained a viable cell count of approximately $9.7 \times 10^8$ CFU/mL.

An antimicrobial solution of nisin and the lactoperoxidase system was prepared and tested as described in Example 1. Samples containing $10^8$ cells per milliliter *E. coli* were withdrawn at 10 and 20 minutes. The results are shown below.

|  | Log$_{10}$ Reduction in Viable Count | |
| --- | --- | --- |
|  | 10 (min) | 20 (min) |
| 20,000 units/mL nisin + LPS | >7 | >7 |
| 20,000 units nisin | 5.37 | 5.91 |
| LPS | 0 | 3.88 |

The effect of the antimicrobial solution containing 20,000 units per milliliter nisin at 10 minutes than would be expected from the additive effect of the nisin or the lactoperoxidase system alone.

*E. coli* (stationary phase)

*Escherichia coli*, ATCC 8739, was maintained on an agar medium containing tryptic soy agar (Difco Labs). Stock agar was prepared as described in Example 1. The overnight culture corresponded to a viable cell count of approximately $3.8 \times 10^9$ cells per mL.

An antimicrobial solution of nisin and lactoperoxidase system was prepared as described in Example 1 and was tested against samples of containing $10^9$ cells per milliliter *E. coli* (stationary phase). Samples were withdrawn after 10, 20, 40, and 60 minute intervals.

Results

|  | Log$_{10}$ Reduction in Viable Count | | | |
| --- | --- | --- | --- | --- |
|  | 10 | 20 | 40 minutes | 60 |
| 20,000 units/mL nisin + LPS | 0 | 4.32 | >7 | >7 |
| 20,000 units/mL nisin | 0 | 0 | 3.1 | 3.54 |
| LPS | 0 | 0 | 0 | 0 |

The effect of the antimicrobial solution was greater than the effect expected from either nisin or LPS alone even on stationary phase microorganisms.

It should be understood that many modifications and variations can be made in the proportions and components used herein without departing from the spirit and scope of the invention, which is solely defined by the claims.

What is claimed is:

1. A synergistic antimicrobial composition comprising of an antimicrobial polypeptide, a hypothiocyanate component and a buffering component capable of providing a pH between about 3 and about 5.

2. The antimicrobial composition of claim 1 wherein the hypothiocyanate component is composed of a peroxidase, a peroxide and a thiocyanate.

3. The antimicrobial composition of claim 1 wherein the antimicrobial polypeptide is chosen from the group consisting of a cecropin, a sarcotoxin, a combination of magainin I and magainin II and a lantibiotic.

4. The antimicrobial composition of claim 1 wherein the peroxidase is lactoperoxidase, the peroxide is hydrogen peroxide and the thiocyanate is sodium or potassium thiocyanate.

5. A method of killing gram-negative organisms on fresh produce, comprising applying the antimicrobial composition of claim 1 at a temperature of at least about 35 degrees centigrade to surfaces of fresh produce.

6. A method of surface disinfection, comprising contacting a surface with a solution of the antimicrobial composition of claim 1 at a temperature of between about 30 and 40 degrees centigrade for between 10 to 60 minutes.

7. A method of killing gram negative organisms, comprising contacting gram negative organisms with the composition of claim 1.

8. A method of killing Salmonella, comprising contacting Salmonella with the composition of claim 1.

9. A method of killing gram-negative organisms, comprising the steps of:
   a. mixing an antimicrobial polypeptide, a hypothiocyanate component and a buffering component capable of providing a pH of between about 3 and 5;
   b. warming the mixture to a temperature of between about 30 and 40 degrees Centigrade; and
   c. contacting the warmed mixture with a surface contaminated with a gram-negative organism for a time sufficient to kill the microorganisms.

10. A method of killing Salmonella on poultry, comprising the steps of:
    a. mixing between 2,000 IU/mL and 20,000 IU/mL nisin, a hypothiocyanate component and a buffering component capable of providing a pH of between about 3 and 5;
    b. warming the mixture to a temperature of about 30 and 40 degrees centigrade with surfaces of slaughter fresh poultry; and
    c. allowing the warm mixture to remain in contact with the poultry surfaces for at least about ten minutes.

11. The method of claim 10 in which the hypothiocyanate component is a thiocyanate, hydrogen peroxide and lactoperoxidase and the ingredients used in step a are mixed in the following order: nisin; thiocyanate; hydrogen peroxide and then lactoperoxidase.

12. A method of producing a synergistic mixture of nisin and a hypothiocyanate component, comprising the steps of:

a. passing a solution of thiocyanate and peroxide over immobilized peroxidase to produce hypothiocyanate;
b. combining the hypothiocyanate produced with between about 2000 IU/mL and 20,000 IU/mL nisin to produce an antimicrobial solution;
c. combining a buffering component capable of providing a pH of between about 3 to 5 with the antimicrobial solution;
d. warming the buffered solution to a temperature of between about 30 and 40 degrees centigrade; and
e. contacting surfaces of slaughter fresh chicken with the mixture for between 10 and 20 minutes.

13. An antimicrobial composition composed of lactoperoxidase, thiocyanate, a peroxide, a buffering component capable of providing a pH from about 3 to about 5 and a synergistic amount is nisin.

* * * * *